US00PP36326P3

(12) United States Plant Patent
Heemskerk

(10) Patent No.: US PP36,326 P3
(45) Date of Patent: Dec. 17, 2024

(54) ***ZAMIOCULCAS* PLANT NAMED 'HEEMSBLA'**

(50) Latin Name: *Zamioculcas zamiifolia*
Varietal Denomination: Heemsbla

(71) Applicant: HEBRU PROJECTEN B.V., De Kwakel (NL)

(72) Inventor: Harold Heemskerk, De Kwakel (NL)

(73) Assignee: HEBRU PROJECTEN B.V., De Kwakel (NL)

( * ) Notice: Subject to any disclaimer, the term of this patent is extended or adjusted under 35 U.S.C. 154(b) by 23 days.

(21) Appl. No.: 18/139,595

(22) Filed: Apr. 26, 2023

(65) Prior Publication Data

US 2024/0365691 P1 Oct. 31, 2024

(51) Int. Cl.
*A01H 5/02* (2018.01)
*A01H 5/12* (2018.01)
*A01H 6/00* (2018.01)
*A01H 6/10* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Zamioculcas* plant named 'Heemsbla', characterized by its compact and upright plant habit with upwardly pointing pinnately-compound leaves; basally clumping habit; vigorous growth habit and moderate growth rate; and glossy leaflets that are dark greyish purple in color and appear almost black in color.

2 Drawing Sheets

Figure 1:
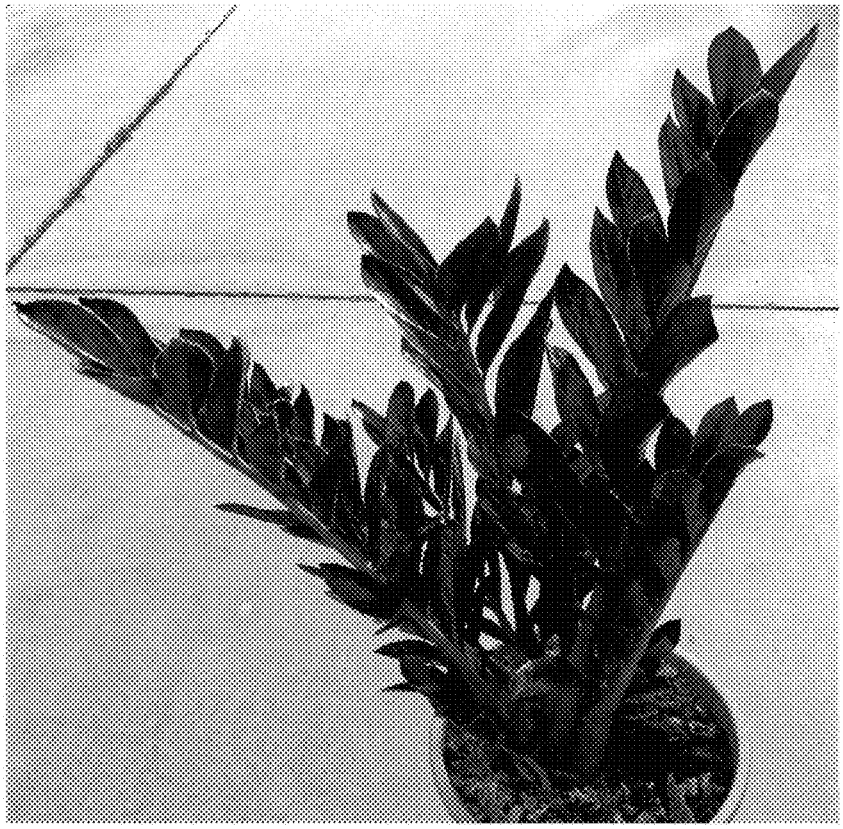

Botanical designation: *Zamioculcas zamiifolia.*
Cultivar denomination: 'HEEMSBLA'.

PRIOR DISCLOSURES BY INVENTOR & APPLICANT/ASSIGNEE

An European Community Plant Breeder's Rights application for the instant plant was filed by the Applicant/Assignee, Hebru Projecten B.V. of De Kwakel, The Netherlands on Feb. 14, 2023, application number 2023/0387. Foreign priority is not claimed to this application.

BACKGROUND OF THE INVENTION

The present invention relates to a new and distinct cultivar of *Zamioculcas* plant, botanically known as *Zamioculcas zamiifolia* and hereinafter referred to by the name 'Heemsbla'.

The new *Zamioculcas* plant is a naturally-occurring branch mutation of *Zamioculcas zamiifolia* 'Heemzamio', disclosed in U.S. Plant Pat. No. 26,262. The new *Zamioculcas* plant was discovered and selected by the Inventor on a single plant from within a population of plants of 'Heemzamio' in a controlled greenhouse environment in De Kwakel, The Netherlands during the summer of 2019.

Asexual reproduction of the new *Zamioculcas* plant by vegetative cuttings in a controlled environment in De Kwakel, The Netherlands since the autumn of 2019 has shown that the unique features of this new *Zamioculcas* plant are stable and reproduced true to type in successive generations of asexual reproduction.

SUMMARY OF THE INVENTION

Plants of the new *Zamioculcas* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Heemsbla'. These characteristics in combination distinguish 'Heemsbla' as a new and distinct *Zamioculcas* plant:

1. Compact and upright plant habit with upwardly pointing pinnately-compound leaves.
2. Basally clumping habit.
3. Vigorous growth habit and moderate growth rate.
4. Glossy leaflets that are dark greyish purple in color and appear almost black in color.

Plants of the new *Zamioculcas* differ from plants of the mutation parent, 'Heemzamio', in leaflet color as plants of the new *Zamioculcas* have dark greyish purple-colored leaflets whereas plants of 'Heemzamio' have dark greyed green and purple-colored leaflets.

Plants of the new *Zamioculcas* can also be compared to plants of *Zamioculcas zamiifolia* 'Dowon', disclosed in U.S. Plant Pat. No. 30,035. In side-by-side comparisons, plants of the new *Zamioculcas* differ from plants of 'Dowon' in the following characteristics:

1. Plants of the new *Zamioculcas* are more compact than plants of 'Dowon'.
2. Plants of the new *Zamioculcas* and 'Dowon' have larger leaflets than plants of 'Dowon'.
3. Developing leaflets of plants of the new *Zamioculcas* are darker green and become darker in color more rapidly than developing leaflets of plants of 'Dowon'.
4. Leaf rachises of plants of the new *Zamioculcas* are green in color whereas leaf rachises of plants of 'Dowon' are close to black in color.

BRIEF DESCRIPTION OF THE PHOTOGRAPHS

The accompanying photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas* plant.

The photograph on the first sheet (FIG. 1) is a side perspective view of a typical plant of 'Heemsbla' grown in a container.

Figure 2:
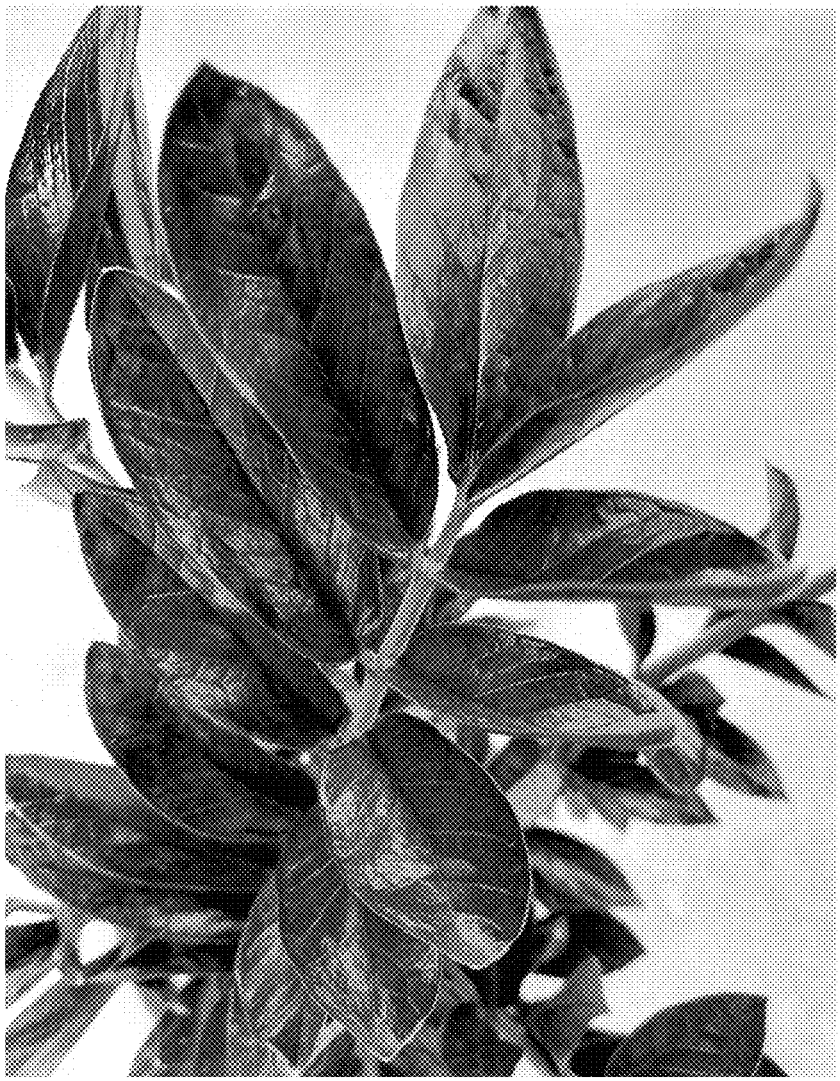

The photograph on the second sheet (FIG. 2) is a close-up view of a typical plant of 'Heemsbla'.

DETAILED BOTANICAL DESCRIPTION

The aforementioned photographs and following observations and measurements describe plants grown during the summer, autumn and winter in 27-cm containers in a glass-covered greenhouse in De Kwakel, The Netherlands and under cultural practices typical of commercial *Zamioculcas* production. During the production of the plants, day temperatures ranged from 20 C to 30 C and night temperatures ranged from 18 C to 26 C. Plants were one year old when the photographs and the detailed description were taken. In the following description, color references are made to The Royal Horticultural Society Colour Chart, 2015 Edition, except where general terms of ordinary dictionary significance are used.

Botanical classification: *Zamioculcas zamiifolia* 'Heemsbla'.

Parentage: Naturally-occurring branch mutation of *Zamioculcas zamiifolia* 'Heemzamio', disclosed in U.S. Plant Pat. No. 26,262.

Propagation:

*Type*.—By vegetative cuttings.

*Time to initiate roots, summer*.—About 21 days at temperatures about 20 C.

*Time to initiate roots, winter*.—About 30 days at temperatures about 20 C.

*Time to produce a rooted young plant, summer*.—About 140 days at temperatures about 20 C.

*Time to produce a rooted young plant, winter*.—About 200 days at temperatures about 20 C.

*Root description*.—Medium in thickness, fleshy; brownish white in color; actual color of the roots is dependent on substrate composition, water quality, fertilizer, substrate temperature and age of roots.

*Rooting habit*.—Moderately freely branching, dense.

Plant description:

*Plant and growth habit*.—Compact and upright plant habit with upwardly pointing leaves; stemless; pinnately compound leaves developing in basal clumps; typically about eight to ten leaves develop per clump; vigorous growth habit and moderate growth rate.

*Plant height*.—About 50 cm to 60 cm.

*Plant diameter*.—About 40 cm.

Leaf description:

*Leaf arrangement*.—Pinnately compound leaves with about 16 to 22 leaflets per leaf.

*Leaflet length*.—About 8 cm to 12 cm.

*Leaflet width*.—About 4 cm.

*Leaflet shape*.—Ovate.

*Leaflet apex*.—Acute.

*Leaflet base*.—Obtuse.

*Leaflet margin*.—Entire.

*Leaflet venation*.—Pinnate.

*Leaflet texture and luster, upper and lower surfaces*.—Smooth, glabrous; glossy.

*Leaflet color*.—Developing leaflets, upper and lower surfaces: Close to 147A. Fully expanded leaflets, upper surface: Close to 202A; venation, close to 202A. Fully expanded leaflets, lower surface: Close to 202A; venation, close to 147A.

*Petioles*.—Length: About 3 mm to 4 mm. Diameter: About 3 mm to 4 mm. Texture: Smooth, glabrous. Color: Close to 147B.

*Leaf rachises*.—Length (soil level to uppermost leaflet): About 50 cm. Length (soil level to lowermost leaflet): About 5 cm to 10 cm. Diameter (at the soil level): About 4 cm. Diameter (just below lowermost leaflet): About 1 cm to 2 cm. Diameter (at uppermost leaflet): About 5 mm. Shape: Cylindrical. Aspect: Mostly upright. Texture and luster: Smooth, glabrous; glossy. Color: Close to 147B.

Inflorescence description: Flower initiation and development has not been observed on plants of the new *Zamioculcas*.

Pathogen & pest resistance: Plants of the new *Zamioculcas* have not been observed to be resistant to pathogens or pests common to *Zamioculcas* plants.

Temperature tolerance: Plants of the new *Zamioculcas* have been observed to be tolerant to temperatures ranging from about 15 C to about 38 C.

It is claimed:

1. A new and distinct *Zamioculcas* plant named 'Heemsbla' as illustrated and described.

* * * * *